United States Patent
Todd et al.

(10) Patent No.: US 10,441,691 B2
(45) Date of Patent: Oct. 15, 2019

(54) FLUID EXTRACTION DEVICE, APPLICATOR DEVICE AND ASSOCIATED METHODS

(71) Applicant: Renephra Limited, Manchester (GB)

(72) Inventors: Simon Todd, Manchester (GB); Ian Middleton, Manchester (GB)

(73) Assignee: Renephra Limited, Manchester (GB)

( * ) Notice: Subject to any disclaimer, the term of this patent is extended or adjusted under 35 U.S.C. 154(b) by 377 days.

(21) Appl. No.: 15/113,249

(22) PCT Filed: Jan. 23, 2015

(86) PCT No.: PCT/GB2015/050164
§ 371 (c)(1),
(2) Date: Jul. 21, 2016

(87) PCT Pub. No.: WO2015/110833
PCT Pub. Date: Jul. 30, 2015

(65) Prior Publication Data
US 2017/0021067 A1 Jan. 26, 2017

(30) Foreign Application Priority Data
Jan. 23, 2014 (GB) .................................. 1401133.2

(51) Int. Cl.
*A61M 1/00* (2006.01)
*A61M 37/00* (2006.01)
(Continued)

(52) U.S. Cl.
CPC ....... *A61M 1/008* (2013.01); *A61B 5/150022* (2013.01); *A61B 5/150099* (2013.01);
(Continued)

(58) Field of Classification Search
CPC .......................... A61B 5/15113; A61K 9/0021
See application file for complete search history.

(56) References Cited

U.S. PATENT DOCUMENTS

| 2002/1007758 | 6/2002 | Lin et al. |
| 2008/0039805 A1* | 2/2008 | Frederickson ....... A61B 17/205 604/272 |

(Continued)

FOREIGN PATENT DOCUMENTS

| JP | 2007-509 706 A | 4/2007 |
| JP | 2011-510779 | 4/2011 |

(Continued)

OTHER PUBLICATIONS

International Application No. PCT/GB2015/050164 International Search Report and Written Opinion, dated May 18, 2015.

(Continued)

*Primary Examiner* — Adam Marcetich
*Assistant Examiner* — Jessica R Arble
(74) *Attorney, Agent, or Firm* — Woodard, Emhardt, Henry, Reeves & Wagner, LLP

(57) ABSTRACT

A device for removing fluid from a body, the device comprising an array of microneedles and a housing; the array of microneedles being disposed within the housing and the housing defining a chamber. The microneedles are moveable between a disengaged position and an engaged position where, in use in the engaged position, the microneedles penetrate the surface of a body. The chamber is adapted to surround the surface of the body through which microneedles penetrate when in the engaged position. The chamber is configured for connection to a vacuum device such that negative pressure can be applied to the chamber.

19 Claims, 5 Drawing Sheets

(51) Int. Cl.
  *A61B 5/15* (2006.01)
  *A61B 5/151* (2006.01)
  *A61B 5/145* (2006.01)
  *A61B 10/00* (2006.01)

(52) U.S. Cl.
  CPC ...... *A61B 5/15113* (2013.01); *A61B 5/15117* (2013.01); *A61B 5/150984* (2013.01); *A61M 1/0039* (2013.01); *A61B 5/14514* (2013.01); *A61B 5/150412* (2013.01); *A61B 2010/008* (2013.01); *A61M 37/0015* (2013.01)

(56) References Cited

U.S. PATENT DOCUMENTS

| | | |
|---|---|---|
| 2011/0172645 A1* | 7/2011 | Moga ................ A61K 9/0021 604/890.1 |
| 2012/0123297 A1 | 5/2012 | Brancazio |
| 2012/0123387 A1* | 5/2012 | Gonzalez .......... A61M 37/0015 604/506 |
| 2012/0277697 A1 | 11/2012 | Haghgooie et al. |
| 2013/0079555 A1 | 3/2013 | Gonzalez-Zugasti et al. |

FOREIGN PATENT DOCUMENTS

| | | |
|---|---|---|
| JP | 2013-521 928 A | 6/2013 |
| WO | WO 2005/0044 333 A2 | 5/2005 |
| WO | WO 2009/098 487 B1 | 8/2009 |
| WO | WO 2011/115602 A1 | 9/2011 |

OTHER PUBLICATIONS

United Kingdom Application No. GB1401133.2 Search Report dated Aug. 11, 2014.
United Kingdom Application No. GB1401133.2 Search Report dated Sep. 16, 2014.
Japan Patent Application No. JP 2016-565577 Office Action dated Oct. 23, 2018 (translation) 7 pages.

* cited by examiner

Figure 4
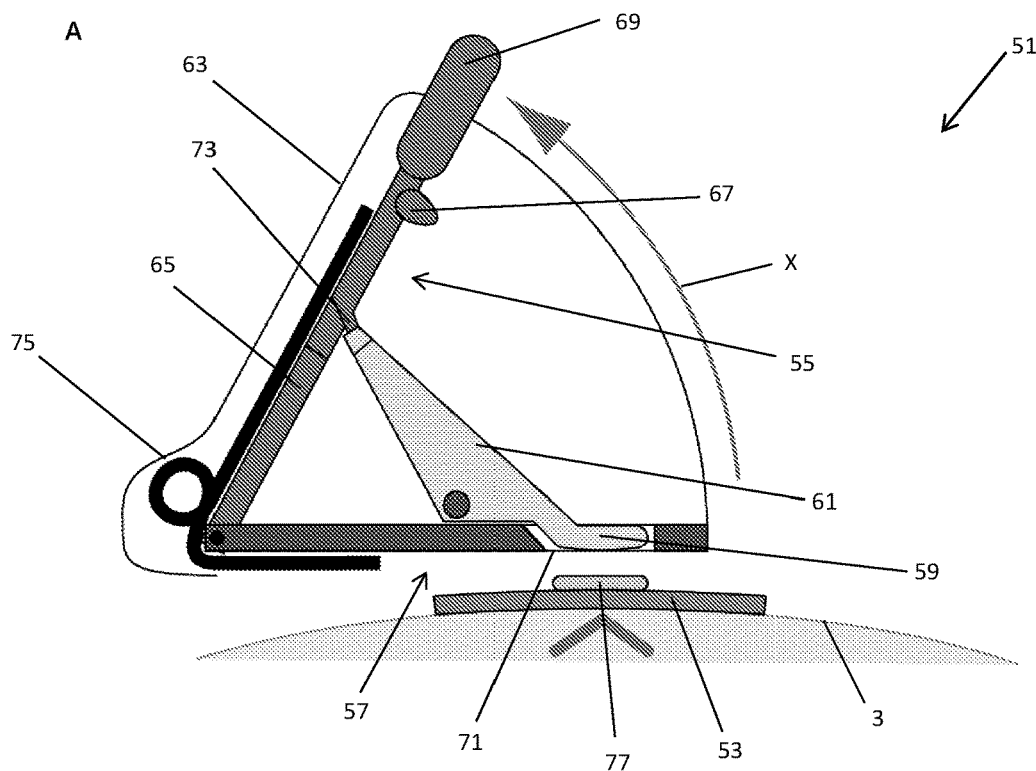
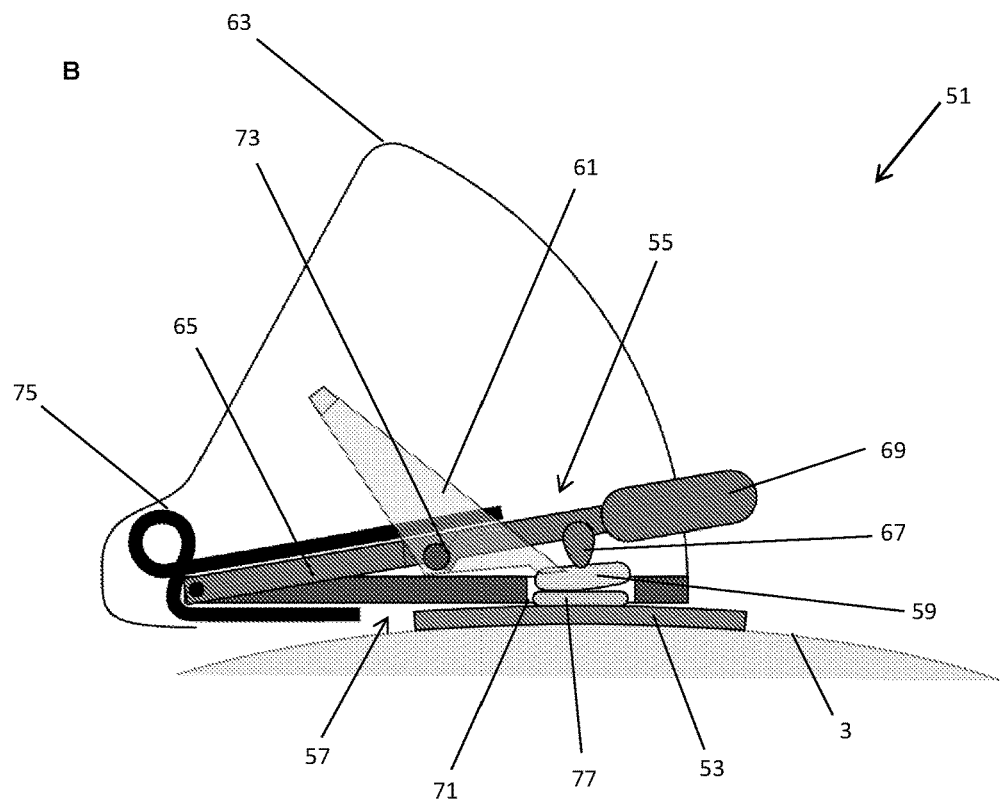

Figure 6
A: Supplied
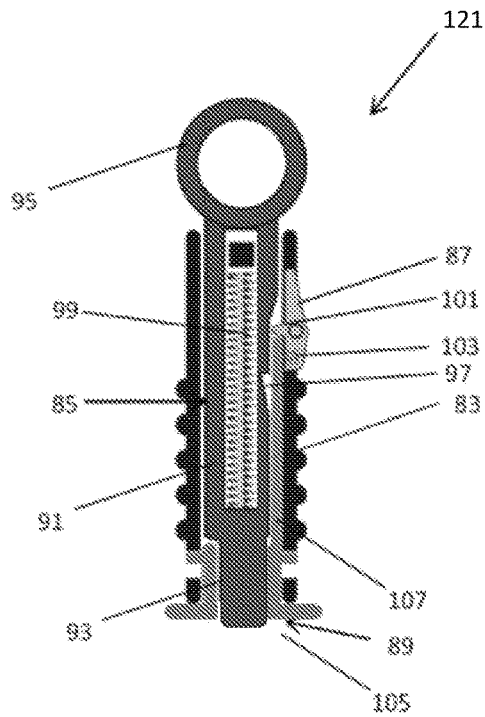
B: Primed
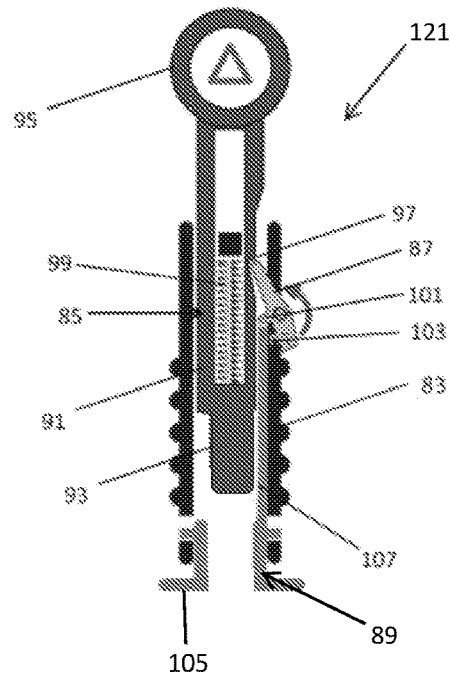
C: Triggered
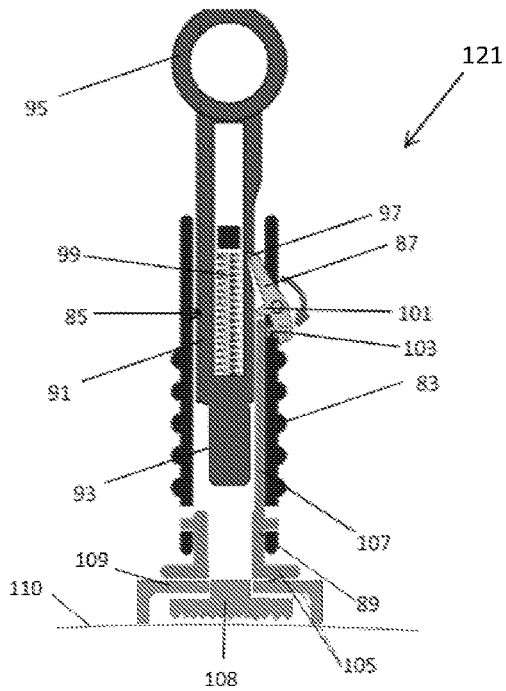
D: Impact
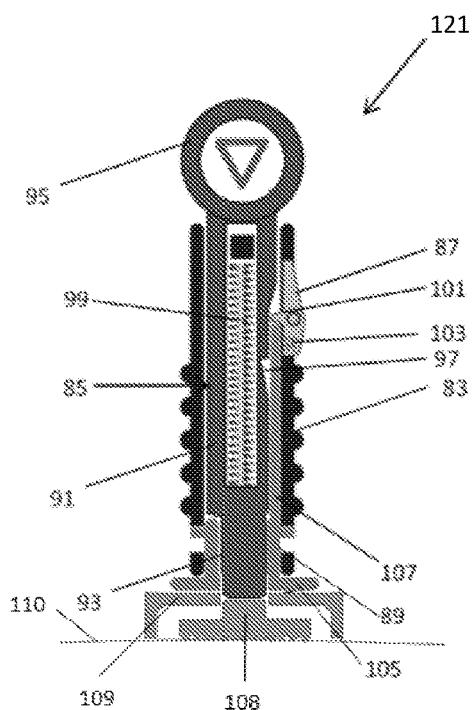

FLUID EXTRACTION DEVICE, APPLICATOR DEVICE AND ASSOCIATED METHODS

The present invention relates to a device for removing fluid from a body and a method for removing fluid from a body, optionally through use of the abovementioned device. The present invention further relates to an applicator for applying a microneedle array to a surface. The devices, and associated materials and methods may find application in the medical field, particularly, but not exclusively in the treatment of fluid overload and oedema arising from conditions such as kidney/renal failure, heart failure, lymphoedema, deep vein thrombosis and cancer.

Native kidneys generate a flow of fluid from the systemic vasculature to the urinary system ending in the bladder prior to voiding. The common and highly generalised view of this function of fluid loss is to rid the body of toxic metabolic waste because in the absence of any renal function death from fluid overload or uraemia ensues within days, uraemia being defined as a medical condition in which kidney function regresses and the kidney fails to excrete into urine the substances that it would otherwise normally have removed, including fluid. As a result of suffering this loss of kidney function excess fluid and uraemic retention products, i.e. substances which are insufficiently removed as a result of the failing kidneys, accumulate.

Loss of kidney function resulting in end-stage renal failure is a major clinical problem with a wide variety of causes. In the UK, over 37,000 people are receiving renal replacement therapy (RRT) at a cost of £1.5 billion per annum (2% of the total NHS budget). With over 5,000 new additions per year, the UK Renal Registry predicts that the number of patients will rise to 60,000 by 2020. Similar increases in incident patients are expected in the developed healthcare systems in the USA and Europe. In the developing world, RRT is highly restricted or absent due to cost and lack of trained healthcare personnel such that renal failure is essentially a death sentence for most. With the developing economies of China and India able to support improved healthcare for their populations, there is potential to treat renal failure in an additional 2-3 billion population providing the therapy can be delivered in a less technological environment and at cheaper cost than currently available.

The current options for renal replacement therapy (RRT) are predominantly only available in healthcare systems of the developed world.

A first option is kidney transplantation. Although transplantation provides a better treatment and quality of life, with a one year survival rate of 97% compared to 84% on dialysis, in the UK only around 1,500 kidneys are available annually, with a transplant waiting list of over 5,000 and growing. Those likely to receive a transplant are younger (median age 49 years, with fewer cardiovascular and other comorbidities) than those on dialysis (peritoneal 58 years, haemodialysis 64 years), which leaves an expanding population of older patients for whom transplantation is not a realistic option.

Current dialysis provision is either haemodialysis or peritoneal dialysis. Haemodialysis involves connecting the patient's blood circulation via a surgically constructed arteriovenous fistula or graft to an external machine that allows removal of low molecular weight metabolites and water across a semi-permeable membrane with return of the "cleansed" blood to the patient. This is predominantly provided in hospital requiring the patient to attend a minimum of 3 days per week (at least 3×4 hour sessions). Significant clinical problems with this modality include failure of vascular access and sepsis and the patient must meet a level of cardiovascular fitness. Quality of life is poor as the patient has to spend 3 days a week in hospital. There is growing evidence of improved patient outcome with frequent or continuous dialysis but this has logistical constraints and is not feasible with current dialysis technology.

Peritoneal dialysis uses the patient's own peritoneal membrane (lining the peritoneal cavity and the visceral organs) as a semi-permeable membrane. With a permanent peritoneal catheter in place, 2 liters of an osmotic solution are infused into the peritoneum and after a 4 hour dwell period, the solution is drained out. Low molecular weight metabolites and water from the myriad blood capillaries in the membrane are driven by the osmotic gradient into the in dwelling dialysis solution. This sequence is repeated 3 or 4 times in a 24 hour period. Automated versions of this modality allow the patient to connect overnight to a machine that provides frequent flushing of the peritoneal cavity.

Significant clinical problems with this modality include failure of the ultrafiltration function of the membrane and excessive membrane scarring which lead to technique failure.

Congestive Heart Failure (CHF) is an inability of the heart to provide sufficient pump suction to maintain blood flow sufficient to meet the needs of the body. Fluid overload is one of the key problems in patients with CHF, whereby excess water and salt accumulate in a patient's body (tissue interstitium) and cause shortness of breath, decreased function of vital organs and swelling of extremities. All this leads to a high rate of hospital admissions of patients with CHF and an increased risk of death.

CHF is a highly prevalent, costly condition that imposes a significant burden on those it affects. Globally, over 26 million people are suffering from CHF and 2 million new cases are diagnosed each year. This number is expected to grow at 8% annually, mainly due to the aging population. The total economic burden of CHF was estimated to be $39.2 billion in 2010 in the US alone.

In addition to improving the heart's performance, CHF treatment aims to remove excess water and sodium (salt) from the body to achieve fluid balance (euvolemia), relieve symptoms and improve the overall quality of life of patients.

Low salt diet, fluid restriction and diuretics are used to reduce fluid volume. However, around 30% of CHF patients experiencing fluid overload do not respond to diuretics. Despite this, many are prescribed large diuretic doses and can suffer from serious adverse effects such as deafness. As a result, many advanced CHF patients are left in a state of chronic fluid retention which leads to increased mortality and morbidity resulting in increased hospital admissions, poor patient performance status and an increased need for drug treatment.

Aquapheresis/ultrafiltration is a relatively new treatment introduced in 2005 and designed to remove fluid in CHF patients who are resistant to diuretics. It is essentially simplified haemodialysis and still relies on access to blood. Up until 2008 there were 15,000 patients treated with this method in 250 clinics worldwide, however, various factors, including the high cost, represent barriers to adoption.

Oedema is the accumulation of fluid in the interstitium which results in observable swelling. Oedema most commonly occurs in the legs and feet where it is referred to as peripheral oedema. There are many causes of oedema including, for example, heart failure, renal failure, liver disease, malnutrition, various medications, for example corticosteroids, lymphoedema, deep vein thrombosis and cancer.

Lymphoedema is a chronic condition that results in swelling of the tissues through fluid overload. Lymphoedema is caused by blockage, damage to or removal of lymph nodes or vessels. In such cases, fluid is unable to pass through the vessels and lymph nodes and consequently lymphatic fluid cannot be drained. This causes the lymphatic system to become overloaded, resulting in fluid build-up and chronic swelling, usually in the extremities. Lymphoedema affects an estimated 100,000 people in the UK and can result in an increased vulnerability to infection and depression.

Many cancer patients suffer from lymphoedema following the surgical removal of lymph nodes or treatment modalities causing damage to the lymphatic system (for example radiotherapy). Lymphoedema can also be caused by infection, injury or trauma (secondary lymphoedema) or genetic mutation (primary lymphoedema).

Lymphoedema and oedema are currently managed through a combination of techniques including the use of compression garments, diet control, light exercise and massage (manual lymphatic drainage). However, there is a need for improved treatment modalities.

Deep vein thrombosis (DVT) is a blood clot that develops in one of the deep veins of the body, often in the leg. Peripheral swelling occurs in up to two-thirds of patients and may be temporary or permanent.

The use of microneedles for various medical purposes has shown increasing promise in recent years. The use of microneedles to puncture the surface of a body, as opposed to conventional needles results in reduced pain and trauma during the puncture process, as microneedles do not penetrate the subcutaneous capillary bed. Microneedles can be applied to body surfaces through manual application (for example, by a medical practitioner). However, for effective microneedle performance, it is important that the microneedles penetrate the skin with accuracy and reproducibility. Although some dedicated microneedle applicators are commercially available (for example, devices containing a trigger button which is pressed by the patient or medical practitioner to apply the microneedles), there is a need for applicators which enable more accurate positioning and reliable application of microneedles, and/or which can reduce the risk of incorrect activation.

An object of the present invention is to obviate or mitigate one or more of the abovementioned problems.

A first aspect of the present invention provides a device for removing fluid from a body, the device comprising:
 i) an array of microneedles; and
 ii) a housing, the array of microneedles being disposed within the housing, and the housing defining a chamber;
 wherein the microneedles are moveable between a disengaged position and an engaged position where, in use in the engaged position, the microneedles penetrate the surface of the body;
 the chamber is adapted to surround the surface of the body through which the microneedles penetrate when in the engaged position; and
 the chamber is configured for connection to a vacuum device, such that negative pressure can be applied to the chamber.

The fluid is preferably interstitial fluid, but the device is not limited exclusively to the removal of interstitial fluid. The use of microneedle arrays, which may comprise solid microneedles, for the purpose of producing punctures on the surface of a body is preferred over the use of a conventional syringe needle as the size of the microneedles minimises pain and trauma during the puncture process by not penetrating the subcutaneous capillary bed. Accordingly, the microneedle height should be up to around 1000 µm or less, preferably around 700 µm or less, preferably around 500 µm or 350 µm, and be capable of creating holes in the stratum corneum of up to around 1000 µm.

The microneedle array may comprise any desirable number of microneedles to suit a particular application. The array may comprise up to around 12000 microneedles, up to around 9000 microneedles, up to around 600 microneedles, or up to around 400 microneedles. Preferably the microneedle array comprises around 5000 microneedles.

The needles in the microneedle array can be arranged substantially symmetrically or alternatively non-symmetrically. By way of example, an array consisting of 100 microneedles may incorporate a symmetrical arrangement of 10×10 needles or a non-symmetrical arrangement of 5×20 needles. The needles can be arranged in arrays of any desirable shape, such as squares, rectangles or circles. By way of example, a preferred embodiment employs a 3 cm diameter circular array of around 5000 microneedles with a microneedle tip-to-tip spacing of around 390 µm, which provides around 7 microneedles per mm$^2$.

The spacing between neighbouring needles in the microneedle array may be substantially uniform throughout the array, or it may vary as desired throughout the array. It should be appreciated that a symmetrical array of needles may be arranged such that the spacing between neighbouring needles is uniform throughout the array, or alternatively the spacing may vary. The fact that the needles are arranged symmetrically does not necessitate uniform spacing between needles, even though this might be preferable in certain embodiments.

Each microneedle within the array can have a straight shaft, a regularly tapered shaft, or a combination of a straight section and a tapered section. Each microneedle may possess a shaft that defines a substantially circular or non-circular cross-section.

The microneedles of the present invention may be hollow or solid. Preferably the microneedles are solid. The solid microneedles may further define one or more external grooves, channels or the like.

The cross-sectional diameter of the base of at least some needles in the array may be around 10 nm to 1 mm, more preferably around 1 µm and 250 µm, and yet more preferably around 10 µm and 200 µm. In a preferred embodiment, the needles in the array have a base diameter of around 160 µm.

The or each microneedle can be manufactured from any appropriate material, such as silicon, glass, metal or plastic and can be micro-engineered to a high degree of precision. The array of microneedles may incorporate a combination of different types of microneedles. By way of example, the array of microneedles may combine microneedles of different heights, inner and/or outer diameters, cross-sectional shapes and spacings between neighbouring microneedles.

The microneedles could be mechanically, electrically, pneumatically or hydraulically driven from the disengaged to the engaged position. For example, activation of a trigger could activate an electric switch which results in a solenoid driving the microneedles from the disengaged position to the engaged position.

In a preferred embodiment of the invention, the microneedles are driven by a manually depressible operating member, which may be mechanically connectable to the microneedle array.

In certain embodiments, it may be desirable to return the microneedles to the disengaged position and to prevent the microneedles returning to the engaged position (i.e. penetrating the body surface) when negative pressure is applied to the chamber. Several mechanisms for returning the microneedles to the disengaged position could be envisaged by the skilled person. Preferred embodiments utilise resilient members which bias the microneedles towards the disengaged position.

In preferred embodiments, the device may comprise resilient members positioned, for example, between the lower roof of the housing and the surface of the body, between the lower surface of the microneedle array and the surface of the body, or in any other suitable position. The presence of these resilient members biases the microneedles to the disengaged position such that the microneedles return to the disengaged position following movement to the engaged position. The resilient member has sufficient inherent resilience that when negative pressure is applied to the chamber, the microneedles do not return to the engaged position, i.e. do not re-penetrate the surface of the body. The resilient member may be a spring (for example a coil spring, torsion spring, leaf spring (for example a living hinge), volute spring or gas spring), an elastomeric member, or any other suitable means. In these embodiments, the operating member may be attached to the microneedle array. Alternatively the operating member may not be attached to the microneedle array, but may be contactable with the microneedle array when a force is applied to the operating member.

In other embodiments, the microneedle array may not be biased towards the disengaged position until after a force has been exerted on the operating means and the microneedles have moved to the engaged position (post-engagement biasing). This post-engagement biasing could occur in a number of ways which would be readily appreciated by the skilled person. For example, post-engagement biasing could result from the microneedle array being coupled to a resilient member following movement to the engaged position. Suitable resilient members are discussed above.

In a preferred embodiment, the resilient member may form part of the operating member. In this specific embodiment, post-engagement biasing is achieved by the operating member (resilient member) and microneedle array not being coupled prior to the exertion of a force upon the operating member. The operating member (resilient member) may be connected to the microneedles only following exertion of said force; this connection may be achieved by connectors positioned on corresponding contactable surfaces of the operating member and/or microneedles. The operating member and/or microneedles may have an adhesive (for example, a pressure sensitive adhesive) on their contactable surfaces. Alternatively the contactable surfaces may comprise complementary connectors, for example male-female connectors, interference fit connectors or other suitable connectors. Specifically, the microneedle array may be coupled to the resilient member via engagement of a connector associated with the microneedle array with a complementary connector associated with or operably linked to the resilient member. Following depression of the operating member, the connectors engage; once the operating member is disengaged, the resilient member biases the microneedles to the disengaged position. The resilient members have sufficient inherent resilience that when negative pressure is applied to the chamber to extract fluid, the microneedles do not return to the engaged position, i.e. do not re-penetrate the surface of the body. Alternatively or additionally, the microneedles may be biased towards their disengaged position by the application of a negative pressure to a suitable space to withdraw the microneedles away from the skin surface.

Return of the microneedles to the disengaged position following penetration functions as a safety feature, as the microneedles are enclosed within the housing, and there is consequently less risk of needle-stick injury during disposal.

The movement of the microneedles from the disengaged position to the engaged position may be achieved by movement of the entire housing. This could be achieved, for example, by the housing being formed of a semi-flexible material. Alternatively, the microneedles may move to the engaged position relative to the housing.

In a further embodiment there is provided a vacuum device connected to the chamber, to exert negative pressure on the chamber. The housing may be configured for attachment of the vacuum device by the presence of a port or other suitable means. The vacuum device may comprise a tank of low-pressure gas, in which case operation of the vacuum device may include opening a valve between the tank and the chamber. As an alternative, the vacuum device may comprise a pump such as a lobe pump, screw pump, piston pump or injector-jet pump (such as a Venturi pump), in which case operation of the vacuum device may include activating the pump. In a preferred embodiment, the vacuum device is a vacuum pump.

Suitable negative pressures which could be exerted on the chamber to enable fluid to be removed from the body are discussed below in relation to the second aspect of the invention.

In one embodiment, the housing comprises a sealing means to enable the housing to be sealed to the surface of the body. This allows the chamber to be hermetically sealed such that on connection of the chamber to a suction device, a vacuum is generated in the chamber surrounding the surface of the body through which the microneedles penetrate. The degree of hermetic sealing required will depend on the application concerned and should not be construed as limiting the scope of this embodiment to completely airtight. The degree of hermetic sealing should, however, be sufficient to obtain and maintain the desired pressure difference during fluid extraction. The sealing means could be, for example, an adhesive layer (e.g. a pressure sensitive adhesive layer) or an elastomeric sealing rim.

In one embodiment, the device may further comprise one or more layers of material positionable onto the body surface prior to application of negative pressure. For instance, a layer of material may be positioned on the underside (i.e. the body-facing side) of the microneedle array such that depression of the microneedle array towards the body surface brings a layer of material into contact with the body. As an alternative, a layer of material may be positioned on the underside of the housing such that the layer of material is brought into contact with the body when the device is positioned on the body. In this embodiment, the microneedles may puncture the layer of material on moving to the engaged position.

The layer of material may be advantageous in that it may protect the skin on application of negative pressure and/or may promote fluid flow from the body via the puncture holes resulting from insertion of the microneedle array. Suitable materials which could be used for the one or more layers of material include an open weave material which would allow the transmission of the negative pressure to the puncture site, such as gauze. Other suitable materials include foam, polymer sheets or fibres, hydrogel sheets or fibres, cellulose or other natural material dressings known to the skilled person. Where more than one layer of material is provided it will be appreciated that the multiple layers may be formed from the same type of material or from different types of material to achieve the desired result.

The device according to the first aspect of the invention may be a single use device. For example, the device may be adapted such that the microneedles may only be moved from the disengaged to the engaged position once. This could be achieved, for example, by return of the microneedle array to the disengaged position resulting in a latch releasing which prevents further movement to the engaged position. Alternatively, a portion of the operating member or microneedle array could be breakable following return of the microneedle array to the disengaged position, to prevent further movement to the engaged position.

In an alternative embodiment, the device could be reusable. For example, the device may be disinfected following use and subsequently reused and/or the microneedle array may be disconnected from the main body of the device, and a replacement microneedle array positioned within the housing. The ability to re-use the device, with or without replacing the microneedle array between uses, may be particularly advantageous when it is necessary to reapply the microneedle array at the same site to which the microneedle array had been previously applied, for example, in circumstances when the device is used over a relatively long period of time (e.g. 4 to 5 hours or more) and at least some of the puncture holes in the skin caused by insertion of the microneedles have closed-up to the extent that fluid flow is no-longer possible via those holes.

It may be desirable to incorporate one or more features into the device of the present invention to prevent re-depression of the microneedle array once it has been applied correctly to the skin surface. A device incorporating such features may represent a "single-use" version of the device, which may be attractive from a safety perspective. When it is desirable to offer a device that can be re-used, the connection/disconnection means, i.e. the connectors described above, may be designed so as to reversibly connect the operating member to the microneedle array. Similarly, a single-use version of the device may incorporate irreversible connectors.

The body is preferably a human or animal body. The microneedle array of the device of the present invention can be applied to any desirable skin surface. In a preferred embodiment, the microneedle array is applied to a lower leg region of the body. The size, shape and/or configuration of the microneedle array incorporated into the device can be selected to suit the particular application site.

The provision of both a vacuum device and an array of microneedles in a single device results in a simplicity which ensures that the vacuum and microneedles are correctly positioned, and consequently, the device can be applied without the aid of a medical practitioner.

A second aspect of the present invention provides a method for removing fluid from a body, the method comprising:
 puncturing a surface of the body; and
 applying a negative pressure to the surface of the body in the region of the punctures to remove fluid from the body via the punctured surface.

The fluid is preferably interstitial fluid, but the method is not limited exclusively to the removal of interstitial fluid. A variety of mechanisms for puncturing the surface of the body can be envisaged, for example, it could be achieved by the application of a microneedle array(s), microneedle roller(s), by electroporation, hydraulic jet, laser, sonic energy, gas jet, projectile or any other suitable means. In a preferred embodiment of the invention the surface of the body is punctured by the application of a microneedle array.

The use of microneedle arrays, which may comprise solid microneedles, for the purpose of producing punctures on the surface of a body is preferred over the use of a conventional syringe needle as the size of the microneedles minimises pain and trauma during the puncture process by not penetrating the subcutaneous capillary bed. Accordingly, the microneedle height (in the microneedle array or microneedle rollers) should be up to around 1000 μm or less, preferably around 700 μm or less, preferably around 550 μm or 350 μm, and be capable of creating holes in the stratum corneum of up to around 1000 μm. The height of the microneedles may be selected based upon the patient. For example, it may be desirable to use shorter microneedles for relatively old or relatively young patients.

Said puncturing of the surface of the body may be effected to expose at least 300 mm$^2$ of tissue, more preferably 500 to 1500 mm$^2$, and most preferably around 565 mm$^2$. This level of tissue exposure could be achieved using a variety of methods, as discussed above. A variety of microneedle types and configurations, could be used to achieve this level of tissue exposure as discussed above in relation to the first aspect of the invention. For example, the microneedles could be closely or widely spaced, dependent on the patient and the level of fluid overload. In one embodiment, a solid microneedle array 3 cm in diameter, with around 5000 microneedles (~550 μm high) is used. The skilled person can easily calculate the exposed tissue surface area using the calculation shown below:

$$\text{Lateral area of a single needle(assumed to be a cone)} = \pi r l = \pi r \sqrt{(r^2 + h^2)}$$

Assuming approximately 80% penetration of the needles and approximately 5000 550 μm microneedles, the total tissue surface area exposed is around 565 mm$^2$.

In a preferred embodiment, the microneedles are removed from the surface of the body prior to application of the negative pressure.

This preferred embodiment of the second aspect of the invention is based, in part, on the surprising finding that by puncturing the surface of a body and applying a negative pressure, significant amounts of fluid can be removed from the body. It would have been expected by the skilled person, that removal of the microneedles would result in the holes in the surface closing rapidly as the skin surface reseals, thus limiting the amount of fluid that could be removed. Surprisingly, it has been determined that if the negative pressure is sufficiently high the holes in the surface will remain open and enable fluid to be removed over a prolonged timespan of hours or even a day or more.

In one embodiment, the method comprises attaching a vacuum device to the region of the body punctured by the microneedles (or other means). The vacuum device may comprise a tank of low-pressure gas, in which case operation of the vacuum device may include opening a valve between the tank and the chamber. As an alternative, the vacuum device may comprise a pump such as a lobe pump, screw pump, piston pump or injector-jet pump (such as a Venturi pump), in which case operation of the vacuum device may include activating the pump. In a preferred embodiment, the vacuum device is a vacuum pump.

The vacuum device may be attached to the skin by a sealing means. For example, the vacuum device may comprise an adhesive, for example a pressure sensitive adhesive, or an elastomeric sealing rim on its body surface contacting face, such that the vacuum device may be hermetically sealed to the surface. The degree of hermetic sealing required will depend on the application concerned and should not be construed as limiting the scope of this embodiment to completely air-tight. The degree of hermetic sealing should, however, be sufficient to obtain and maintain the desired pressure difference during fluid extraction.

The negative pressure applied should be one suitable to remove the desired volume of fluid from the body. The negative pressure may be applied continually or intermittently over the period of time during which fluid flows from the body via the puncture holes made by insertion of the microneedles into the skin. The skilled person would be able to determine the appropriate magnitude of the negative pressure and whether continual or intermittent application of negative pressure would be appropriate based on the patient, and the severity of fluid overload. In one embodiment said negative pressure is around 25 to around 500 mmHg, more preferably around 50 to around 500 mmHg, more preferably around 100 to around 300 mmHg, more preferably around 200 mmHg.

An appropriate rate of fluid removal for a particular patient will depend upon many factors known to the skilled person. For example, a fluid rate of removal of up to around 2000 ml/day may be appropriate, more preferably up to around 1000 ml/day, or around 500 ml/day. An appropriate lower limit for the rate of fluid removal may be at least around 10 ml/day, more preferably around 50 ml/day or more preferably around 100 ml/day. For various therapeutic applications, a preferred lower limit for the rate of fluid removal is around 220 ml/day. The skilled person will appreciate that the specific rate and amount of fluid to be removed should be determined taking into account patient-specific factors including height, weight, amount of excess fluid, comorbidities etc.

Similarly, an appropriate fluid flow rate for a particular patient will depend upon many factors known to the skilled person. An appropriate fluid flow rate may be around 0.25 to around 4 ml/cm$^2$/hr, more preferably around 1 to around 3 ml/cm$^2$/hr, more preferably around 2 ml/cm$^2$/hr.

The location on the body appropriate for puncturing will depend upon many factors known to the skilled person. For example, the site of fluid overload, the health of the patient, the health of the proposed skin site(s) to which the microneedles are intended to be applied, the site of the oedema, the position of the patient, e.g. application to a lower limb if the patient is standing or sitting, or the back if lying down.

The method may be used to remove any desirable body fluid, but it is preferred that the fluid is interstitial fluid or at least one component thereof. For example, said at least one component of the interstitial fluid is preferably selected from the group consisting of water, a uraemic toxin, a metabolic product, a salt and an ion.

The method may further comprise applying a layer of material onto the punctured body surface prior to application of the vacuum device. One or more layers of such material may be applied onto the punctured body surface prior to application of the vacuum device. The application of this layer or these layers of material is not essential for the method of the present invention; however, it may serve to protect the skin on application of the vacuum device and may promote fluid flow. Suitable materials which could be used include an open weave material which would allow the transmission of the negative pressure to the puncture site, such as gauze. Other suitable materials include foam, polymer sheets or fibres, hydrogel sheets or fibres, cellulose or other natural material dressings known to the skilled person. When more than one layer of material is provided it will be appreciated that the multiple layers may be formed from the same type of material or from different types of material to achieve the desired result.

In one embodiment, the method includes use of the device according to the first aspect of the invention (and any embodiment thereof described in this specification).

There is further provided a method of treating fluid overload or oedema comprising the method of the second aspect of the invention. Said fluid overload or oedema may result from a number of conditions, including, but not limited to kidney/renal failure, heart failure, lymphoedema, deep vein thrombosis and cancer.

An example of a protocol which has been successfully used to achieve removal of fluid from the body using the abovementioned method of is shown below:

1. An appropriate skin antiseptic is applied to the insertion site on the skin of the patient.
2. A microneedle array is applied to the skin. This can be achieved in a variety of ways, for example manual insertion or by use of a microneedle applicator.
3. The microneedles are removed from the skin and discarded.
4. A piece of gauze is placed over the microneedle insertion site. The gauze should be large enough to cover all the punctures created by the microneedles and also should be larger than the vacuum assembly, to offer additional protection to the skin.
5. A vacuum tubing unit with pressure sensitive adhesive is applied to the site of microneedle insertion, ensuring an airtight seal around the puncture site.
6. The vacuum tube is connected to a collection canister and vacuum pump set to 50-500 mmHg.
7. Fluid flows through the vacuum tubing into the collection canister.
8. Steps 2-9 are repeated as required.
9. The vacuum tubing unit is removed from the puncture site.
10. An appropriate skin antiseptic is applied to the wound site.

Modification of this basic protocol could be envisaged by the skilled person dependent on the patient and severity of fluid overload. For example, the following steps could be varied:

The gauze can be removed from the skin;

A variety of vacuum pressures could be utilised; and/or

The number and type of microneedles could be varied.

An in vitro model of the method according to the second aspect of the invention resulted in the following data being obtained. The model consisted of a hydrophilic polyurethane foam with a thin hydrophobic polyurethane membrane bonded to the surface of the foam. Pore size of the foam was 20 to 400 μm. The foam was wrapped around a plastic tube to simulate a limb size and shape, and fixed into place. The foam was hydrated with saline solution containing bovine serum albumin to represent the interstitial fluid. Microneedles were used to penetrate the 'skin' (membrane) and then the protocol/procedure above was used.

TABLE 1

| Experiment no. | Pressure (mmHg) | Fluid extracted (g/hour) |
| --- | --- | --- |
| 1 | 100 | 18.6 |
| 2 | 200 | 29.4 |
| 3 | 350 | 47.9 |

Utilising the abovementioned protocol, the following in vivo data has been collected:

TABLE 2

| Patient no. | Sex | Age | Weight (kg) | Oedema severity | Pressure (mmHg) | Microneedles | Fluid extracted (g/hour) |
| --- | --- | --- | --- | --- | --- | --- | --- |
| 1 | M | 63 | 102 | Moderate | 200 | 550 μm solid | 20 |
| 2 | F | 89 | 57.5 | Moderate | 200 | 550 μm solid | 22.4 |
| 3 | M | 43 | 66 | Tense | 100 | 550 μm solid | 12 |

Research trials have been performed on a group of patients suffering from "visible" oedema due to heart and/or kidney failure or chronic peripheral oedema of unknown aetiology. 83 patients underwent tests to access and extract epidermal interstitial fluid (ISF). A total of 144 interventions were performed.

Two access methods were tested: solid microneedle arrays and small hollow hypodermic needles.

Microneedle Arrays

Pre-fabricated solid polymethylmethacrylate (PMMA) microneedle arrays were used. Two different types of arrays were tested: one with microneedles 550 μm in height and 170 μm base and another with microneedles 350 μm in height and 177 μm base. The 550 μm array had a diameter of 3 cm with an active surface area of 7.1 cm$^2$ containing 5491 microneedles. The 350 μm array had a diameter of 1.6 cm with an active area of 2 cm$^2$ containing 1316 microneedles.

After skin antisepsis, the microneedles were applied on the dorsum of the foot or the medial aspect of the shin using a purpose designed microneedle spring loaded applicator (see description below in relation to the applicator of the present invention).

Hypodermic Needles 22 or 23 gauge hypodermic needles were used as an alternative access method to ISF. After skin antisepsis and a lidocaine 1% spray, the needle was inserted at 30-45° to about half its length.

Once access was gained into the epidermal interstitial compartment through puncture of the stratum corneum, fluid removal was enhanced by the application of a negative pressure using a KCl ActiVAC® negative pressure unit over the microneedle application area immediately after removal of the microneedles. The ActiVAC® delivers adjustable negative pressures of 25 to 200 mmHg, i.e. pressures of −25 to −200 mmHg, with the extracted fluid collected via tubing into changeable canisters with a capacity of 300 ml. The pressure was gradually increased to achieve a target negative pressure of up to 200 mmHg, i.e. a target pressure of −200 mmHg, which was maintained during the fluid removal. Fluid removal lasted 1-4 hours and at the end of the session, the volume of interstitial fluid removed during the session was measured.

Data was analysed using GraphPad Prism® 6.04. Parametric and non-parametric data were expressed as mean±SD and median and range or interquartile range (IOQR) respectively. Student t tests, Fisher exact tests, Mann Whitney tests and Pearson correlation coefficients were used for statistical analyses, with a probability of 0.05 or less considered statistically significant.

Successful ISF Extraction

Of the 144 ISF extractions, 1 ml or more of ISF was extracted in 49%, 5 ml of more in 25% and 10 ml or more in 14%.

Spontaneous "Meaningful Flow" of ISF

Comparison of microneedle and non-microneedle access in terms of producing spontaneous "meaningful flow" of ISF (i.e. a sufficient volume that can be reliably collected and measured) showed microneedles to be superior. Microneedle access achieved spontaneous "meaningful flow" of ISF (i.e. a sufficient volume that can be reliably collected and measured) in 55% of cases while non-microneedle access produced this in 10% of cases. Microneedle arrays with 550 μm tall microneedles achieved significantly higher mean ISF volumes than those with 350 μm tall microneedles (7±12 ml versus 0.5±1 ml; p<0.0001).

Enhancing Flow of ISF: Negative Pressure

The use of a negative pressure suction device resulted in 5 ml or more of fluid in 27% of interventions. The mean volume of ISF extracted in these cases was 24±9 ml over an average of 2.3 hours giving a mean flow rate of 11 ml per microneedle array per hour for an average vacuum pressure of −192 mmHg. A positive correlation between the negative pressure exerted and the total ISF was observed (r=0.42, p=0.03; FIG. 7).

Sustaining ISF Extraction: Time

The volume of ISF extracted also showed a linear correlation with the duration of extraction time (r=0.24, p=0.008; FIG. 8).

Patient Characteristics

No correlation was observed between the class of oedema (i.e. acute/sub-acute versus chronic) and the volume of extraction (p=0.10). Similarly, clinical tenseness or compliance of oedema showed no correlation with the volume of extraction (r=0.05; p=0.003).

Pain, Bleeding and Skin Integrity

During the extractions, a 0-10 analogue pain score questionnaire was administered as well as a scale of "comfort" of the whole set up ('comfortable', 'uncomfortable' or 'very uncomfortable'). Blood spots and skin erythema were also noted. A 0-7 skin irritation score was administered immediately after microneedle removal, one hour after and 24 hours after wherever possible (i.e. with inpatients).

82% of patients reported a pain score of 2 or less with microneedles, with 62% reporting no pain at all during the insertion of microneedles. The mean pain score for microneedles was 1.1±2 (median=0, IQR 0-2). The mean pain score for hypodermic needles, despite being inserted after use of lidocaine spray, was 1.9±3 (median=0, IQR 0-4). After microneedle insertion, once the device was left in place, 96% of patients found it to be 'comfortable' or 'very comfortable'. In 83% of cases, no visible skin irritation was present after device removal, whilst mild erythema was present in 14% of cases. Two cases of significant erythema presented after device removal (irritation score of 4 and 5 out of 7 respectively). After one hour and 24 hours, evidence of device application was visible in only three cases. These three patients had developed blisters, which resolved with no complications within 72 hours. There was one case of cellulitis after microneedle application; this resolved with antibiotics.

Microneedle access with negative pressure and a high Bioratio could achieve ISF extraction rates of 2 ml/cm$^2$/hr which equates to 800 ml over 4 hours using a 10×10 cm skin surface.

These results demonstrate the utility of the devices and methods of the first and second aspects of the invention in removing fluid from patients suffering from conditions which result in excess fluid accumulation.

A third aspect of the present invention provides an applicator for applying a microneedle array to a surface, the applicator comprising:
 a pressure element to contact a contact element associated with a microneedle array to be applied to a surface; and
 a hammer configured to be driven from a primed position to an impact position to deliver an impulse to the pressure element or the microneedle array, wherein
the pressure element is operably connected to the hammer whereby exertion of a force on the pressure element allows the hammer to be driven from the primed position to the impact position.

It will be appreciated that the applicator is not limited for use solely with "microneedles arrays"; it may be used to apply any type of cutting or puncturing element to a surface in a controlled, reliable manner.

In one embodiment of the third aspect of the invention, the contact element is the rear of the microneedle array.

In a further aspect of the invention there is provided an applicator for applying a microneedle array to a surface, the applicator comprising:
 a pressure element to contact a microneedle array to be applied to a surface; and
 a hammer configured to be driven from a primed position to an impact position to deliver an impulse to the pressure element, wherein
the pressure element is operably connected to the hammer whereby exertion of a force on the pressure element allows the hammer to be driven from the primed position to the impact position.

In a yet further aspect of the invention there is provided an applicator for applying a microneedle array to a surface, the applicator comprising:
 a pressure element to contact a microneedle array to be applied to a surface; and
 a hammer configured to be driven from a primed position to an impact position to deliver an impulse to the microneedle array, wherein
the pressure element is operably connected to the hammer whereby exertion of a force on the pressure element allows the hammer to be driven from the primed position to the impact position.

In an embodiment of the applicator of the present invention, the pressure element contacts a contact element associated with a microneedle array, for example a housing in which the microneedle array is disposed. One advantage of this arrangement is that initial contact of the pressure element to the housing does not inadvertently result in application of the microneedles to the surface. The skilled person will appreciate that the pressure element could contact any suitable contact element or surface associated with the microneedle array which allows an impulse to be delivered to the microneedle array or pressure element following triggering of the applicator.

In an embodiment, the hammer, when driven to the impact position, may deliver an impulse directly to the rear of the microneedle array. In an alternative, the hammer may deliver an impulse to the microneedle array via the pressure element.

In a preferred embodiment of the applicator of the present invention, the hammer is biased towards the impact position and is retainable in the primed position by a latch element. The pressure element may be connected to the hammer via the latch element. In a preferred embodiment, the exertion of a force on the pressure element results in the latch element being disturbed thereby releasing the hammer.

The hammer may be biased towards the impact position in any suitable fashion. For example, it may be biased by an active actuator such as a hydraulic or pneumatic cylinder, or an electric linear actuator such as a solenoid. Instead or in addition, the hammer may be biased by a resilient element such as a spring (for instance a coil spring, torsion spring, leaf spring, volute spring or gas spring), or an elastomeric member.

In one embodiment the pressure element is integral to the latch element. Alternatively, the pressure element may be a separate entity to the latch element, and may be connected to the latch element.

The hammer may move from the primed position to the impact position along an arcuate path. Alternatively, the hammer may move from the primed position to the impact position along a linear path, or any other suitable path which will enable a force sufficient for application of the microneedles to the surface to be imparted onto the pressure element or the microneedle array.

The applicator may optionally contain a counting means, to enable the user to determine how many times the applicator has been deployed. This may be useful as an indication of the shelf life of the device. This could be achieved, for example, through incorporation of a simple mechanical counter, which is moved on by a unit when the hammer is moved from the impact position to the primed position. The presence of a counting device allows the quality of microneedle application achieved through use of the applicator to be maintained.

In one embodiment of the invention, the pressure element may be adapted for complementary engagement with the microneedle array (or contact element associated therewith), so that the applicator is triggered only when complementary engagement with the microneedle array is achieved. This prevents the hammer being driven until correctly positioned thus resulting in improved quality and/or accuracy of microneedle application. The complementary engagement means may, for example, include a portion of the rear of a microneedle array with a dome-shaped construction engaging with a corresponding dome-shaped recess on the pressure element, or vice versa. Other complementary shapes or suitable engagement means would be readily appreciated by the skilled person. For example, one or both contacting surfaces defined by the pressure element and the microneedle array (or contact element associated therewith) may be provided with adhesive to reversibly or irreversibly bond the pressure element and microneedle array together. Prior to use, the adhesive may be protected under a release paper, which is removed only when it is desired to activate the device.

A further aspect of the invention comprises a device incorporating an applicator comprising:

a pressure element to contact a contact element associated with a microneedle array to be applied to a surface; and
a hammer configured to be driven from a primed position to an impact position to deliver an impulse to the pressure element or microneedle array, wherein the pressure element is operably connected to the hammer whereby exertion of a force on the pressure element allows the hammer to be driven from the primed position to the impact position;
in combination with a microneedle array.

The applicator described in the abovementioned aspects of the invention (and any embodiment thereof described in this specification) would be eminently suitable for use as the device incorporating an applicator as described above.

In a further aspect there is provided a device incorporating an applicator comprising:
a pressure element to contact a microneedle array to be applied to a surface; and
a hammer configured to be driven from a primed position to an impact position to deliver an impulse to the pressure element, wherein the pressure element is operably connected to the hammer whereby exertion of a force on the pressure element allows the hammer to be driven from the primed position to the impact position;
in combination with a microneedle array.

In one embodiment of the device incorporating an applicator, the microneedle array (or contact element associated therewith) and the pressure element are adapted for complementary engagement. In one embodiment a portion of the rear of a microneedle array may have a recess which engages with a corresponding projection on the pressure element of the applicator, or vice versa. Other complementary shapes and suitable engagement means as discussed above would be readily appreciated by the skilled person.

In a further embodiment of the device incorporating an applicator, the microneedle array may comprise a device according to the first aspect of the invention (and any embodiment thereof described in this specification). The rear of the microneedle array (or contact element associated therewith) of the device according to the first aspect of the invention and the pressure element of the applicator may be adapted for complementary engagement such that the applicator is triggered only when intended and when complementary engagement with the microneedle array is correctly achieved, thereby offering a fail-safe arrangement which prevents mis-firing and incorrect alignment of the pressure element with the microneedle array.

A yet further aspect of the invention provides a method of applying a microneedle array to a surface employing a device incorporating:
a pressure element to contact a contact element associated with a microneedle array to be applied to a surface; and
a hammer configured to be driven from a primed position to an impact position to deliver an impulse to the pressure element or microneedle array, wherein the pressure element is operably connected to the hammer whereby exertion of a force on the pressure element allows the hammer to be driven from the primed position to the impact position, the method comprising:
applying the pressure element to the contact element associated with the microneedle array to release the hammer to deliver an impulse to the microneedle array or pressure element and thereby applying the microneedles to the surface.

In one embodiment, the contact element is the rear of the microneedle array.

A further aspect provides a method of applying a microneedle array to a surface employing a device incorporating:
a pressure element to contact a microneedle array to be applied to a surface; and
a hammer configured to be driven from a primed position to an impact position to deliver an impulse to the pressure element, wherein the pressure element is operably connected to the hammer whereby exertion of a force on the pressure element allows the hammer to be driven from the primed position to the impact position, the method comprising:
applying the pressure element to the microneedle array to release the hammer to deliver an impulse to the pressure element and thereby applying the microneedles to the surface.

In an alternative, the pressure element contacts a contact element associated with a microneedle array, for example a housing in which the microneedle array is disposed. One advantage of this arrangement is that initial contact of the pressure element to the housing does not inadvertently result in application of the microneedles to the surface. The skilled person will appreciate that the pressure element could contact any suitable contact element or surface associated with a microneedle array which allows an impulse to be delivered to the microneedle array or pressure element following triggering of the applicator.

In an embodiment, the hammer, when driven to the impact position, may deliver an impulse directly to the rear of the microneedle array. In an alternative, the hammer may deliver an impulse to the microneedle array via the pressure element.

The applicator of the present invention would be eminently suitable for use in the method described above.

Embodiments of the present invention will now be described, by way of example only, with reference to the accompanying figures.

Figure 5:
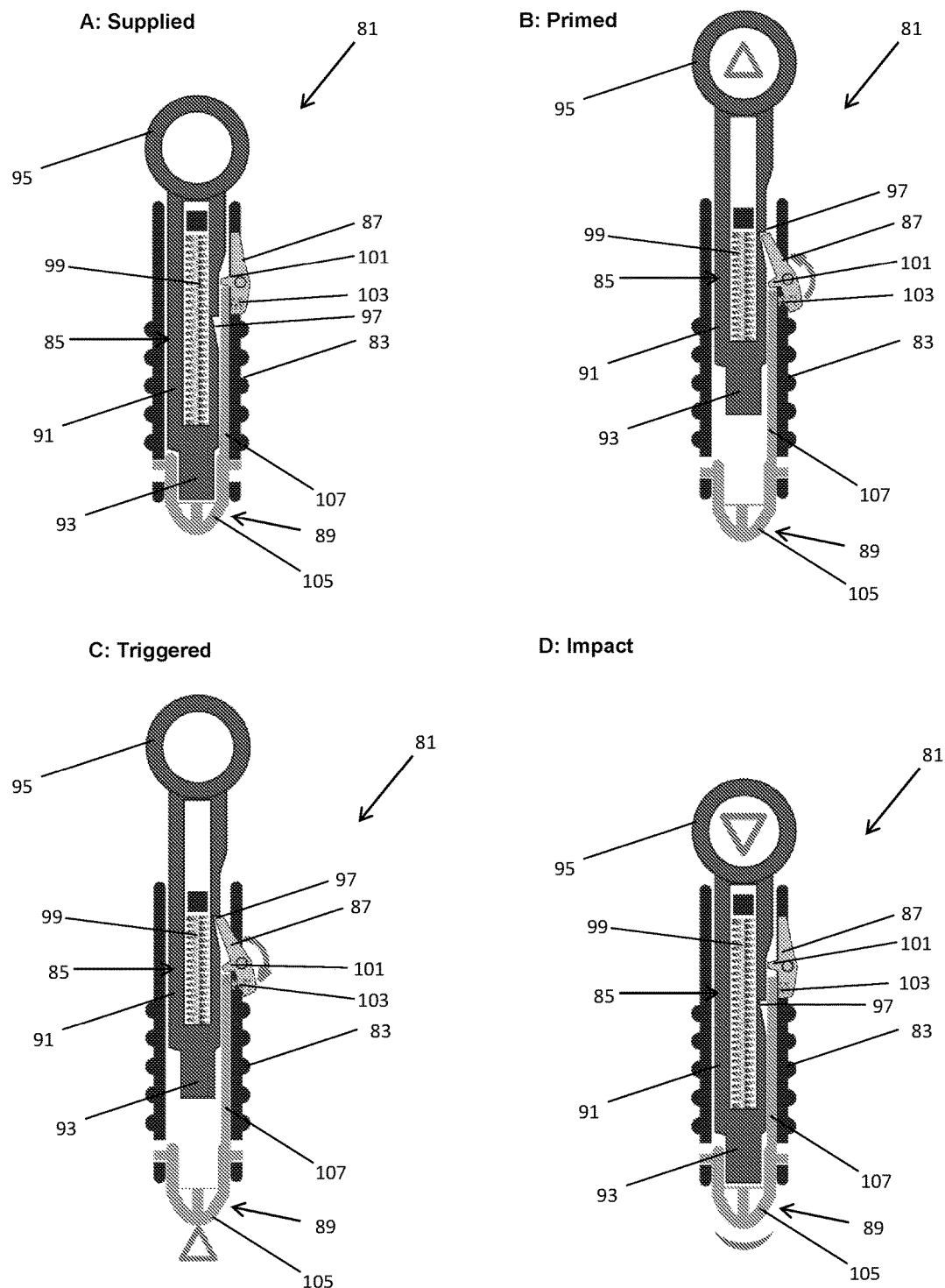

FIGS. 4A and 4B are schematic representations of a device according to a preferred embodiment of the applicator of the present invention which could be used in the method of applying a microneedle array to a surface according to the invention, or could be used to apply the device of the first aspect of the invention to the skin. The device is shown in a primed configuration (FIG. 4A) and in an impact configuration (FIG. 4B);

FIGS. 5A to 5D are schematic representations of a device according to an alternative embodiment of the applicator of the present invention which could be used in the method of applying a microneedle array to a surface according to the invention, or could be used to apply the device of the first aspect of the invention to the skin. The device is shown in a configuration as stored/supplied prior to use (FIG. 5A), a primed configuration ready for use (FIG. 5B), a triggered configuration (FIG. 5C) and an impact configuration (FIG. 5D);

FIGS. 6A to 6D are schematic representations of a device according to an alternative embodiment of the applicator of the present invention which could be used in the method of applying a microneedle array to a surface according to the invention, or could be used to apply the device of the first aspect of the invention to the skin. The device is shown in a configuration as stored/supplied prior to use (FIG. 6A), a primed configuration ready for use (FIG. 6B), a triggered configuration (FIG. 6C) and an impact configuration (FIG. 6D).

Figure 7:
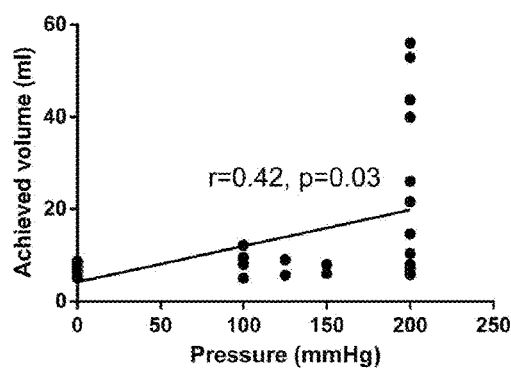

FIG. 7 shows the correlation of extracted ISF volume of 5 ml or more with negative pressure. A linear relationship between the applied negative pressure and the total volume extracted was observed.

Figure 8:
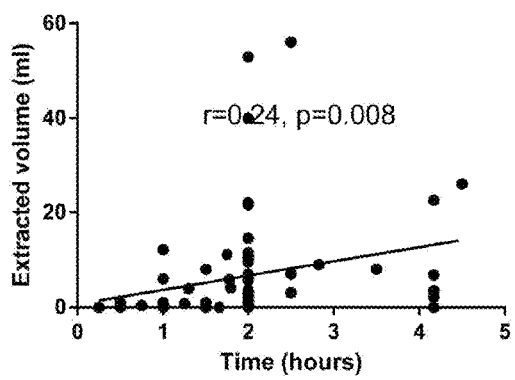

FIG. 8 shows the correlation between extracted ISF volume and length of extraction. The total volume of ISF extracted correlated with the duration of the extraction in all sessions during which microneedles were used as access method with a negative pressure to enhance extraction.

Figure 1:
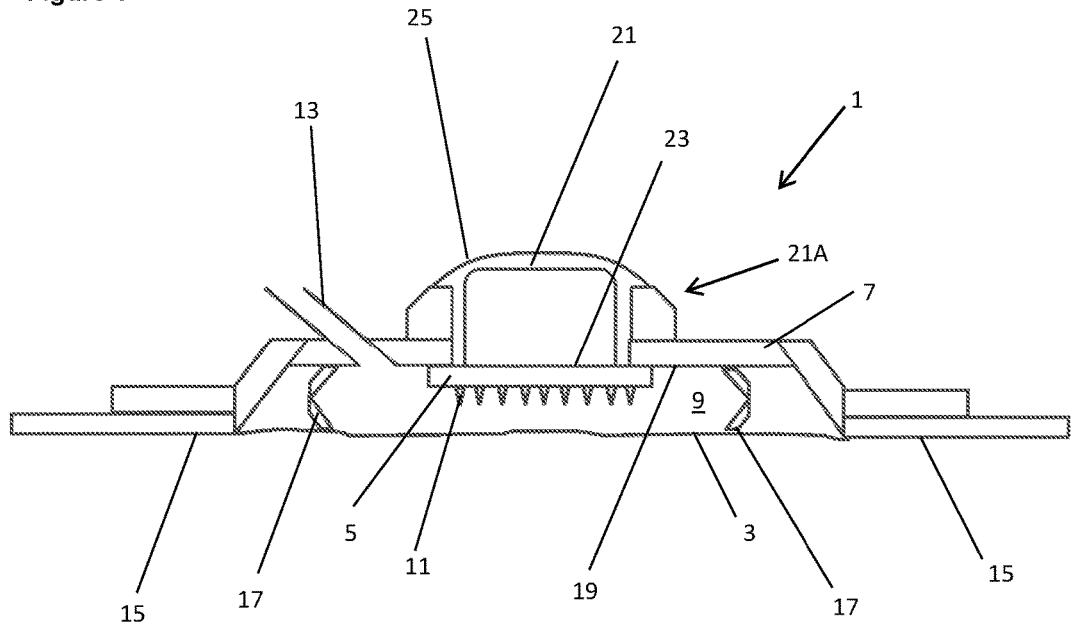
FIG. 1 is a schematic representation of a device according to a preferred embodiment of the first aspect of the present invention which could be used in the method according to the second aspect of the invention, or applied to the skin using the applicator of the invention.

Referring to FIG. 1, there is depicted schematically a device 1, which can be employed to remove fluid from a body, according to a preferred embodiment of the first aspect of the invention. The device 1 is shown positioned on a skin surface 3 of a human body (not shown). The device 1 incorporates an array of microneedles 5 positioned substantially parallel to the skin surface 3 within a housing 7, the housing 7 defining a chamber 9. Each needle 11 in the array 5 is around 550 μm in height. The housing 7 defines a port 13 configured for connection to a vacuum device (not shown) such that negative pressure can be applied to the chamber 9. An adhesive (not shown) is provided on a skin contacting surface 15 of the housing 7 to allow the housing 7 to be hermetically sealed to the skin surface 3. The device 1 further incorporates two resilient living hinges 17 positioned between a lower surface 19 of the housing 7 and the skin surface 3. An operating member, or button, 21 is connected to a rear surface 23 of the microneedle array 5, and extends backwards therefrom, such that an upper portion 21A of the button 21 lies above the housing 7. A diaphragm 25 is positioned over the upper portion of the button 21 and is connected to the housing 7 either side of the button 21.

When it is desired to use the device 1, the skin surface 3 to which the device 1 will be applied is wiped with a bacteriocidal solution and the device 1 positioned against the skin surface 3. A vacuum device (not shown) is attached to the port 13 by means of tubing (not shown). A downward force (which could be applied by the patient themselves, a medical practitioner, or a dedicated microneedle applicator device) is exerted upon the button 21 which results in the movement of the microneedle array 5 downwards from the disengaged position (as shown in FIG. 1) to the engaged position, where the microneedles 11 penetrate the skin 3. The device 1 of FIG. 1 is made of a semi-flexible material such that on depression of the button 21 the entire body of the housing 7 flexes towards the surface of the skin 3 such that the microneedles 11 penetrate the skin surface 3. The downwards force exerted on the button 21 results in the living hinges 17 flexing outwardly. On removal of the downwards force from the button 21, the resilience of the living hinges 17 causes them to expand back to their original conformation, lifting the microneedle array 5 off the skin surface 3 and returning the microneedle array 5 to the disengaged position as shown in FIG. 1. The vacuum device is activated, such that a negative pressure is applied to the chamber 9. The living hinges 17 have sufficient inherent resilience that upon application of a sufficient negative pressure to the chamber 9 to drive fluid flow from the body (described in more detail below), the microneedle array 5 does not drop down to the engaged position against the skin surface 3 despite the inherent flexibility of the housing 7.

Application of a negative pressure to the chamber 9, results in interstitial fluid being extracted from the body via holes made by the microneedles 11 penetrating the skin surface 3. The fluid is passed via the port 13 and vacuum tubing (not shown) to a storage canister (not shown). When sufficient interstitial fluid has been removed from the body, the vacuum is deactivated and the device 1 removed from the surface of the skin 3. The entire device 1 may be disposed of, or alternatively, the microneedle array 5 may be removed from the device, and a new microneedle array 5 applied for subsequent re-use of the device 1.

Figure 2:
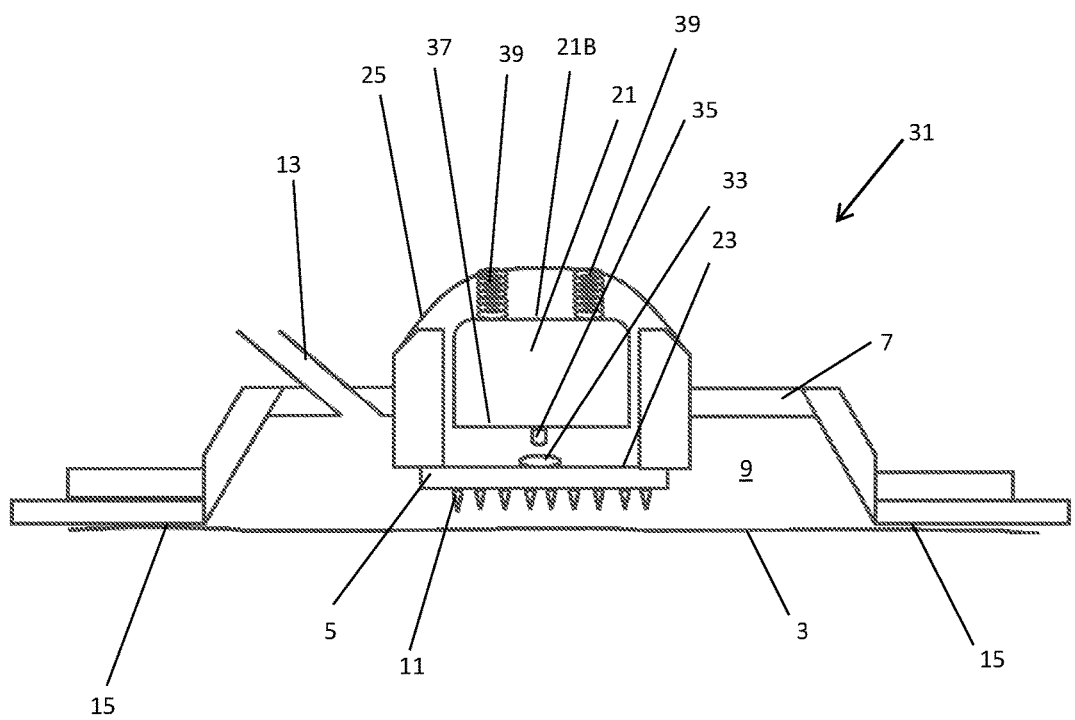
FIG. 2 is a schematic representation of a device according to another preferred embodiment of the first aspect of the present invention which could be used in the method according to the second aspect of the invention, or applied to the skin using the applicator of the invention.

Referring to FIG. 2, there is depicted schematically a device 31, which can be employed to remove interstitial fluid from a body, according to another preferred embodiment of the first aspect of the invention. The device 31 is shown positioned on a skin surface 3 of a human body (not shown). Similar to the device 1 shown in FIG. 1, the device 31 incorporates an array of microneedles 5 positioned substantially parallel to the skin surface 3 within a housing 7, the housing 7 defining a chamber 9. Each needle 11 in the array is around 550 μm in height. The housing 7 defines a port 13 configured for connection to a vacuum device (not shown) such that negative pressure can be applied to the chamber 9. An adhesive (not shown) is provided on a skin contacting surface 15 of the housing 7 to allow the housing 7 to be hermetically sealed to the skin surface 3. An operating member, or button, 21 is positioned above the microneedle array 5 and extends vertically, such that an upper portion 21A of the button 21 is located above the housing 7. The button 21 is connectable to the rear of the microneedle array 23 by way of connectors 33, 35 positioned on an upper surface 23 of the microneedle array 9 and a lower surface 37 of the button 21 respectfully. Positioned between the top 21B of the button 21 and a diaphragm 25 are springs 39. The diaphragm 25 is positioned over the top 21B of the button 21 and the springs 39 and is connected to the housing 7 either side of the button 21.

When in use, the device 31 is positioned on the skin surface 3 through which fluid is to be extracted. A vacuum device (not shown) is attached to the port 13 by means of tubing (not shown). A downward force (which could be applied by the patient themselves, a medical practitioner, or a dedicated microneedle applicator device) is exerted upon the button 21 which moves the button 21 through the housing 7 towards the microneedle array 5. This movement results in connection of the button 21 with the microneedle array 5 via connectors 33, 35. Following connection of the button 21 with the microneedle array 5 the microneedle array 5 moves downwards from the disengaged position (as shown in FIG. 2) to an engaged position, where the microneedles 11 penetrate the skin surface 3. The device 31 of FIG. 2 is made of a rigid material such that when the downward force is exerted on the button 21, the button 21 moves downwards through the housing 7 before contacting the microneedle array 5, which it then drives towards the skin surface 3.

The downwards force exerted on the button 21 results in the springs 39 being stretched. On removal of the downwards force from the button 21, the springs 39 return to their original conformation. This results in the button 21 returning to its original position, and the microneedle array 5 returning to the disengaged position (as shown in FIG. 2) by virtue of its connection to the button 21 via the connectors 33, 35. The vacuum device is activated, such that a negative pressure is applied to the chamber 9. The springs 39 have sufficient inherent resilience that, upon application of the negative pressure to the chamber 9, the microneedle array 5 does not return to the engaged position where the microneedles 7 penetrate the skin surface 3.

Application of a negative pressure to the chamber 9, results in interstitial fluid being extracted from the body via holes in the skin made by the microneedles 11 penetrating the skin surface 3. The interstitial fluid is passed via the port 13 and vacuum tubing (not shown) to a storage canister (not shown). When sufficient interstitial fluid has been removed from the body, the vacuum can be deactivated and the device 31 removed from the surface of the skin 3. The entire device 31 may be disposed of, or alternatively, the connectors 33, 35 may be disengaged and the microneedle array 5 removed from the device 31, and replaced by a new microneedle array 5 for future use.

Figure 3:
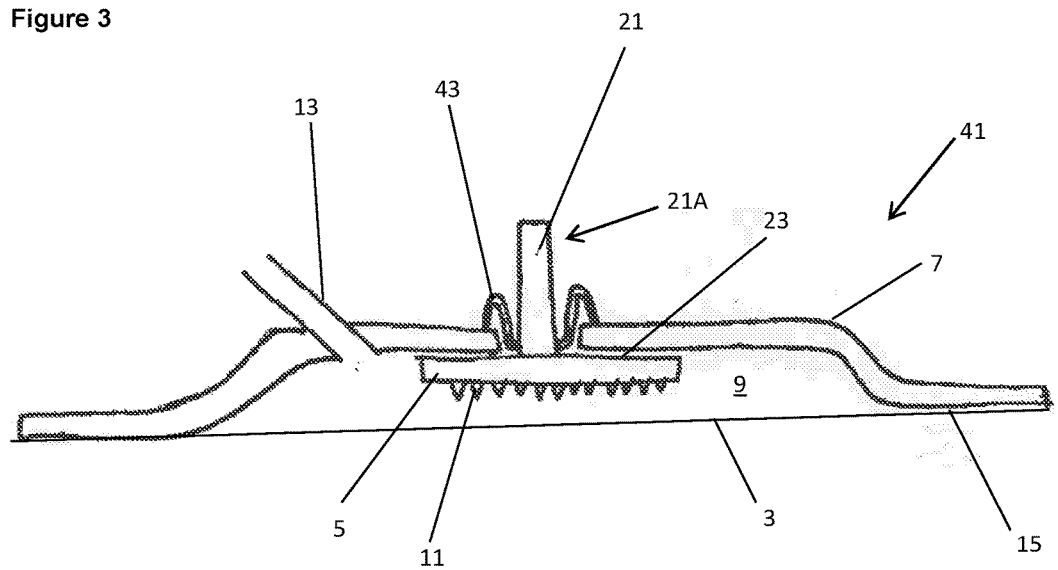
FIG. 3 is a schematic representation of a device according to another preferred embodiment of the first aspect of the present invention which could be used in the method according to the second aspect of the invention, or applied to the skin using the applicator of the invention.

Referring to FIG. 3, there is depicted schematically a device 41, which can be employed to remove interstitial fluid from a body, according to another preferred embodiment of the first aspect of the invention. The device 41 is shown positioned on a skin surface 3 of a human body (not shown). Similar to the device 1 shown in FIG. 1, the device 41 incorporates an array of microneedles 5 positioned substantially parallel to the skin surface 3 within a housing 7, the housing 7 defining a chamber 9. Each needle 11 in the array is around 550 μm in height. The housing 7 defines a port 13 configured for connection to a vacuum device (not shown) such that negative pressure can be applied to the chamber 9. An adhesive (not shown) is provided on a skin contacting surface 15 of the housing 7 to allow the housing 7 to be hermetically sealed to the skin surface 3. An operating member 21 is connected to a rear surface 23 of the microneedle array 5, and extends backwards therefrom, such that an upper portion 21A of the operating member 21 lies above the housing 7. A diaphragm 43 connects the operating member (in this case the upper portion 21A of the operating member 21) to the housing 7. The diaphragm 43 is positioned to seal the boundary between the housing 7 and operating member 21 so as to prevent leakage through the boundary when the vacuum is engaged.

When it is desired to use the device 41, the skin surface 3 to which the device 41 will be applied is wiped with a bacteriocidal solution and the device 41 positioned against the skin surface 3. A vacuum device (not shown) is attached to the port 13 by means of tubing (not shown). A downward force (which could be applied by the patient themselves, a medical practitioner, or a dedicated microneedle applicator device) is exerted upon the operating member 21 which results in the movement of the microneedle array 5 downwards from the disengaged position (as shown in FIG. 3) to the engaged position, where the microneedles 11 penetrate the skin 3.

The diaphragm 43 of FIG. 3 is made of a flexible resilient material such that on depression of the operating member 21 the diaphragm 43 flexes, allowing the operating member 21 to move towards the surface of the skin 3. On removal of the downwards force from the operating member 21, the resilience of the diaphragm 43 causes the operating member 21 to move back to its original position, lifting the microneedle array 5 off the skin surface 3 and returning the microneedle array 5 to the disengaged position as shown in FIG. 3. The vacuum device is activated such that a negative pressure is applied to the chamber 9.

The operating member 21 has a sufficiently small diameter such that, combined with the resilience of the diaphragm 43, upon application of a sufficient negative pressure to the chamber 9 to drive fluid flow from the body (described in more detail below), the microneedle array 5 does not drop down to the engaged position against the skin surface 3.

Application of a negative pressure to the chamber 9, results in interstitial fluid being extracted from the body via holes made by the microneedles 11 penetrating the skin surface 3. The fluid is passed via the port 13 and vacuum tubing (not shown) to a storage canister (not shown). When sufficient interstitial fluid has been removed from the body, the vacuum is deactivated and the device 41 removed from the surface of the skin 3. The entire device 41 may be disposed of, or alternatively, the microneedle array 5 may be removed from the device 41, and a new microneedle array applied for subsequent re-use of the device 41.

Referring now to FIGS. 4A and 4B, there is depicted schematically an applicator device 51 according to a preferred embodiment of the applicator of the invention which can be used to apply microneedles to a surface. The device 51 is shown positioned above a skin surface 3 of a human body (not shown) onto which a microneedle array 53 has been placed. The device 51 incorporates a hammer 55, a base plate 57, a pressure element 59 and a latch 61 located within a housing 63.

The hammer 55 is attached to the base plate 57. On release of the latch 61, the hammer 55 can move between a primed position (shown in FIG. 4A) and an impact position (shown in FIG. 4B) where it impacts the pressure element 59.

The hammer 55 comprises an elongate shaft 65 and an impact member 67 located towards the end of the shaft 65 furthest from the base plate 57. An operating handle 69 and a notch 73 for engagement with the latch 61 also form part of the hammer 55. The hammer 55 is pivotally connected to the base plate 57 via the opposite end of the shaft to that which the impact member 67 in connected. The hammer 55 further comprises a spring 75 which biases the hammer 55 towards the impact position (shown in FIG. 4B).

To prime the device 51 ready for use, a user retracts the hammer 55 away from the base plate in the direction of arrow X. When in the primed position as shown in FIG. 4A, the latch 61 engages with the notch 73, retaining the hammer 55 in the primed position.

The base plate 57 defines an opening 71 through which the pressure element 59 can project (or within which the pressure element 59 can reside) to engage the underlying microneedle array 53. When placed on top of the microneedle array 53, the pressure element 59 engages with engagement button 77 on the rear of the microneedle array 53. On engagement of the pressure element 59 with the engagement button 77, the latch element 61 pivots anti-clockwise to release the latch element 61 from the notch 73 and thereby release the hammer 55, and the spring 75 drives the hammer 55 from the primed position to the impact position.

The skilled person will appreciate that in an alternative, the pressure element could engage with any suitable element or surface associated with the microneedle array, for example a housing in which the microneedle array is disposed or directly contact the rear of the microneedle array.

Following movement of the hammer 55 from the primed position to the impact position, the impact member 67 of the hammer 55 exerts a force on the rear of the pressure element 59 which force is subsequently transferred to the engagement button 77 and microneedle array 53, thereby applying the microneedles (not shown) to the skin surface 3.

Referring now to FIGS. 5A-D, there is depicted schematically an applicator device 81 according to a preferred embodiment of the applicator of the invention which can be used to apply microneedles to a surface. The device 81 is shown in four configurations: A: Supplied; B: Primed; C: Triggered; and D: Impact. In this embodiment of the applicator of the invention, the device 81 comprises an elongate tubular housing 83 containing a hammer 85, a latch 87 and a pressure element 89.

The hammer 85 is moveable within the housing 83 from a primed position (shown in FIG. 5B) to an impact position (shown in FIG. 5D) where the hammer 85 impacts the pressure element 89 (described more fully below).

The hammer 85 is concentrically disposed within the housing 83 and comprises an elongate shaft 91, an impact member 93 located at one end of the shaft 91, an operating handle 95 located at the opposite end of the shaft 91 and a notch 97 for engagement with the latch 87. The hammer 85 further comprises a spring 99 which biases the hammer 85 towards the impact position in which the impact member 93 is in contact with the pressure element 89 (shown in FIG. 5D).

The hammer 85 is moveable axially relative to the housing 83 away from the pressure element 89 towards a primed position (shown in FIG. 5B). When in the primed position, the latch 87 engages with the notch 97 to retain the hammer 85 in the primed position against the biasing force of the spring 99. Disengagement of the latch 87 releases the hammer 85 which is driven by the spring 99 to the impact position.

The latch 87 is pivotally attached to the housing 83 and defines an inwardly projecting knob 101 which projects into the housing 83. When the hammer 85 is retracted to the primed position by a force exerted on the operating handle 95, the latch 87 pivots anticlockwise and engages the notch 97, thereby maintaining the hammer 85 in the primed position. The latch 87 is biased towards engagement with the notch 97 by means of a spring 103. The pivoting of the latch 87 also results in the knob 101 contacting the pressure element 89 and moving the pressure element 89 downwards relative to the housing 83 into a primed position (described in more detail below).

The pressure element 89 comprises a dome-shaped contact portion 105 for contacting the rear of a microneedle array (not shown) and an elongate portion 107 extending within the housing 83 whose upper end contacts the knob 101 of the latch 87. The dome-shaped contact portion 105 projects out of the housing 83 at the end which is proximate the impact member 93 when the hammer 85 is in the engaged position. The pressure element 89 can move axially relative to the housing 83 between an inactive position (shown in FIG. 5A) and a primed position (shown in FIG. 5B). This movement between inactive and primed positions results from movement of the hammer 85 upwards relative to the housing 83 to the primed position, which allows the latch 87 to pivot anticlockwise and the knob 101 to force down the elongate portion 107.

The dome-shaped contact portion 105 of the pressure element 89 is configured to engage with the rear of a microneedle array (not shown). When the contact portion 105 comes into contact with the microneedle array, the elongate portion 107 moves axially upwards relative to the housing 83 which pivots the latch 87 via contact of the elongate position 107 of the pressure element 89 with the knob 101. This leads to release of the hammer 85, which is subsequently driven by the spring 99 from the primed to the impact position. When in the impact position, the impact member 93 of the hammer 85 exerts a force on the rear of the pressure element 89 which force is subsequently transferred to the rear of the microneedle array, thereby applying the microneedles to the skin.

When in use, the hammer 85 is moved to the primed position through exertion of a force being applied to the operating handle 95. Said force could, for example, be applied by the patient or a medical practitioner. Exertion of said force and subsequent movement of the hammer 85 results in the latch 87 engaging with the notch 97 which maintains the hammer 85 in the primed position without continued application of said force. The device 81 is then positioned in the region of a microneedle array (not shown) applied to the skin surface of a body (not shown). The pressure element 89 is applied to the rear of the microneedle array, which results in the latch 87 pivoting and releasing the hammer 85 from the primed position. The spring 99 drives the hammer 85 towards the engaged position where the impact member 93 exerts a force on the rear of the pressure element 89 which force is transferred to the microneedle array, thereby applying the microneedles to the skin.

Referring now to FIGS. 6A-D there is depicted schematically an applicator device 121 according to a preferred embodiment of the applicator of the invention which can be used to apply microneedles to a surface. The device 121 is shown in four configurations: A: Supplied; B: Primed; C: Triggered; and D: Impact. This embodiment of the applicator of the invention is similar to the embodiment shown in FIGS. 5A-D and so the same reference numbers shall be used in FIGS. 6A-D as are used above in relation to the same features in the embodiment shown in FIGS. 5A-D. The device 121 comprises an elongate tubular housing 83 containing a hammer 85, a latch 87 and a pressure element 89.

The hammer 85 is moveable within the housing 83 from a primed position (shown in FIG. 6B) to an impact position (shown in FIG. 6D) where the hammer 85 impacts a microneedle array 108 (described more fully below).

The hammer 85 is concentrically disposed within the housing 83 and comprises an elongate shaft 91, an impact member 93 located at one end of the shaft 91, an operating handle 95 located at the opposite end of the shaft 91 and a notch 97 for engagement with the latch 87. The hammer 85 further comprises a spring 99 which biases the hammer 85 towards the impact position in which the impact member 93 is in contact with the microneedle array 108, in use (shown in FIG. 6D).

The hammer 85 is moveable axially relative to the housing 83 away from the pressure element 89 towards a primed position (shown in FIG. 6B). When in the primed position, the latch 87 engages with the notch 97 to retain the hammer 85 in the primed position against the biasing force of the spring 99. Disengagement of the latch 87 releases the hammer 85 which is driven by the spring 99 to the impact position.

The latch 87 is pivotally attached to the housing 83 and defines an inwardly projecting knob 101 which projects into the housing 83. When the hammer 85 is retracted to the primed position by a force exerted on the operating handle 95, the latch 87 pivots anticlockwise and engages the notch 97, thereby maintaining the hammer 85 in the primed position. The latch 87 is biased towards engagement with the notch 97 by means of a spring 103. The pivoting of the latch 87 also results in the knob 101 contacting the pressure element 89 and moving the pressure element 89 downwards relative to the housing 83 into a primed position (described in more detail below).

The pressure element 89 comprises a contact portion 105 for contacting the rear of a housing 109 for a microneedle array 108, and an elongate portion 107 extending within the housing 83 whose upper end contacts the knob 101 of the latch 87. The contact portion 105 projects out of the housing 83 at the end which is proximate the impact member 93 when the hammer 85 is in the engaged position. The pressure element 89 can move axially relative to the housing 83 between an inactive position (shown in FIG. 6A) and a primed position (shown in FIG. 6B). This movement between inactive and primed positions results from movement of the hammer 85 upwards relative to the housing 83 to the primed position, which allows the latch 87 to pivot anticlockwise and the knob 101 to force down the elongate portion 107.

The contact portion 105 of the pressure element 89 is configured to engage with the rear of a housing 109 for the microneedle array 108. When the contact portion 105 comes into contact with the housing 109 for the microneedle array 108, the elongate portion 107 moves axially upwards relative to the housing 83 which pivots the latch 87 via contact of the elongate position 107 of the pressure element 89 with the knob 101. This leads to release of the hammer 85, which is subsequently driven by the spring 99 from the primed to the impact position. When in the impact position, the impact member 93 of the hammer 85 exerts a force on the rear of the microneedle array 108 which force applies the microneedles to the skin 110.

When in use, the hammer 85 is moved to the primed position through exertion of a force being applied to the operating handle 95. Said force could, for example, be applied by the patient or a medical practitioner. Exertion of said force and subsequent movement of the hammer 85 results in the latch 87 engaging with the notch 97 which maintains the hammer 85 in the primed position without continued application of said force. The device 81 is then positioned in the region of a microneedle array 108 positioned within a housing 109 applied to the skin surface of a body 110. The pressure element 89 is applied to the housing 109 for the microneedles 108, which results in the latch 87 pivoting and releasing the hammer 85 from the primed position. The spring 99 drives the hammer 85 towards the engaged position where the impact member 93 exerts a force on the rear of the microneedle array 108 which force applies the microneedles to the skin 110.

It will be appreciated that the novel features of the different embodiments of the devices described above with reference to FIGS. 1 to 6 may be employed individually as described above or any two or more novel features may be employed together in the same device.

It will be appreciated that references to particular directions and orientations (top, rear, downwards etc.) are used simply for convenience and are not intended to be in any way limiting.

The invention claimed is:

1. A device for removing fluid from a body, the device comprising:
   i) an array of microneedles;
   ii) a housing, the array of microneedles being disposed within the housing, and the housing defining a chamber; and
   iii) an applicator for applying the array of microneedles to a surface, wherein the applicator includes a pressure element to contact a contact element associated with the array of microneedles, the contact element being the housing, and a hammer configured to be driven from a primed position to an impact position to deliver an impulse to the pressure element,
   wherein the pressure element is operably connected to the hammer whereby exertion of a force on the pressure element allows the hammer to be driven from the primed position to the impact position.

2. The device of claim 1, wherein the microneedles are moveable between a disengaged position and an engaged position where, in use in the engaged position, the microneedles penetrate the surface of a body;
   the chamber is adapted to surround the surface of the body through which the microneedles penetrate when in the engaged position; and
   the chamber is configured for connection to a vacuum device, such that negative pressure can be applied to the chamber.

3. The device according to claim 2 wherein the array of microneedles is biased towards the disengaged position.

4. The device according to claim 3 wherein the device further comprises one or more resilient members which bias the array of microneedles towards the disengaged position.

5. The device according to claim 3 wherein the array of microneedles is biased towards the disengaged position after a force has been exerted on the operating means and the microneedles have moved to the engaged position.

6. The device according to claim 4 wherein the array of microneedles is coupled to the resilient member following movement to the engaged position.

7. The device according to claim 6 wherein the array of microneedles is coupled to the resilient member via engagement of a connector associated with the microneedle array with a complementary connector associated with or operably linked to the resilient member.

8. An applicator for applying a microneedle array to a surface, the applicator comprising:
   a pressure element to contact a contact element associated with a microneedle array to be applied to a surface; and
   a hammer configured to be driven from a primed position to an impact position to deliver an impulse to the pressure element,
   wherein the pressure element is operably connected to the hammer whereby exertion of a force on the pressure element allows the hammer to be driven from the primed position to the impact position.

9. The applicator according to claim 8 wherein the contact element is the rear of the microneedle array.

10. The applicator according to claim 8 wherein the contact element is a housing in which the microneedle array is disposed.

11. A device incorporating an applicator according to claim 8 in combination with a microneedle array.

12. A method of applying a microneedle array to a surface employing a device according to claim 8 the method comprising:
   applying the pressure element to a contact element associated with a microneedle array to release the hammer to deliver an impulse to the pressure element and thereby applying the microneedles to the surface.

13. The applicator according to claim 8 wherein the hammer is biased towards the impact position, and is retainable in the primed position by a latch element.

14. The applicator according to claim 13 wherein the pressure element is connected to the hammer via the latch element.

15. The applicator according to claim 14 wherein the exertion of said force causes the latch element to be disturbed, thereby releasing the hammer.

16. The applicator according to claim 8 wherein the hammer is biased towards the impact position by a resilient element.

17. The applicator according to claim 8 wherein the pressure element is integral to a latch element.

18. The applicator according to claim 8 wherein the hammer moves from the primed position to the impact position along an arcuate path or a linear path.

19. The applicator according to claim 8 wherein the pressure element is adapted for complementary engagement with the contact element associated with the microneedle array, so that the applicator is triggered only when complementary engagement with the contact element associated with the microneedle array is achieved.

\* \* \* \* \*